United States Patent [19]

Maclean et al.

[11] Patent Number: 5,719,191

[45] Date of Patent: Feb. 17, 1998

[54] 1,1,2-TRIPHENYLBUT-1-ENE DERIVATIVES FOR TREATING ALZHEIMER'S DISEASE

[75] Inventors: David B. Maclean, Providence, R.I.; David D. Thompson, Gales Ferry, Conn.

[73] Assignee: Pfizer Inc., New York, N.Y.

[21] Appl. No.: 805,039

[22] Filed: Feb. 21, 1997

[51] Int. Cl.$^6$ ................................................ A61K 31/135
[52] U.S. Cl. ........................................................ 514/648
[58] Field of Search ............................................ 514/648

[56] References Cited

U.S. PATENT DOCUMENTS

| | | | |
|---|---|---|---|
| 5,047,431 | 9/1991 | Schickaneder et al. | 514/648 |
| 5,254,594 | 10/1993 | Niikura et al. | 514/648 |
| 5,384,332 | 1/1995 | Fontana | 514/648 |
| 5,441,986 | 8/1995 | Thompson | 514/648 |
| 5,455,275 | 10/1995 | Fontana | 514/648 |
| 5,550,164 | 8/1996 | Fontana | 514/648 |

FOREIGN PATENT DOCUMENTS 0659418  6/1995  European Pat. Off. ..... A61K 31/445

OTHER PUBLICATIONS

Honjo, H., et al., "Senile Dementia–Alzheimer's Type and Estrogen," *Morm. metab. Res.* 27 (1995) 204–207.

*Primary Examiner*—Jerome D. Goldberg
*Attorney, Agent, or Firm*—Peter C. Richardson; Gregg C. Benson; Mervin E. Brokke

[57] ABSTRACT

The present invention provides novel methods of inhibiting Alzheimer's Disease comprising administering to a human in need of treatment an effective amount of a compound of formula I

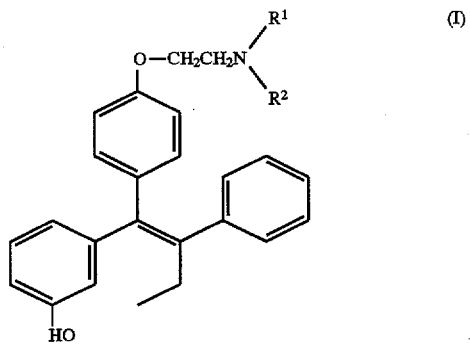

wherein $R^1$ and $R^2$ may be the same or different provided that, when $R^1$ and $R^2$ are the same, each is a methyl or ethyl group, and, when $R^1$ and $R^2$ are different, one of them is a methyl or ethyl group and the other is hydrogen or a benzyl group; or a pharmaceutically acceptable salt thereof.

3 Claims, No Drawings

1,1,2-TRIPHENYLBUT-1-ENE DERIVATIVES FOR TREATING ALZHEIMER'S DISEASE

This is a continuation of provisional application 60/025,201 filed Feb. 28, 1996, the benefit of which is hereby claimed under 37 C.F.R. §1.78(a)(3).

BACKGROUND OF THE INVENTION

Alzheimer's Disease (AD) is a degenerative brain disorder characterized clinically by progressive loss of memory, cognition, reasoning, judgment and emotional stability that gradually leads to profound mental deterioration and ultimately death. AD is a common cause of progressive mental failure (dementia) in aged humans and is believed to represent the fourth most common medical cause of death in the United States. AD has been observed in varied races and ethnic groups worldwide and presents a major present and future public health problem. The disease is currently estimated to affect about two to three million individuals in the United States alone. To date, AD has proven to be incurable.

The brains of individuals with AD exhibit neuronal degeneration and characteristic lesions variously referred to as amyloidogenic plaques, vascular amyloid angiopathy, and neurofibrillary tangles. Large numbers of these lesions, particularly amyloidogenic plaques and neurofibrillary tangles, are generally found in several areas of the human brain important for memory and cognitive function in patients with AD. Smaller numbers of these lesions in a more restricted anatomical distribution are found in the brains of most aged humans who do not have clinical AD. Amyloidogenic plaques and vascular amyloid angiopathy also characterize the brains of individuals with Trisomy 21 (Down's Syndrome) and Hereditary Cerebral Hemorrhage with Amyloidosis of the Dutch-Type (HCHWA-D). At present, a definitive diagnosis of AD usually requires observing the aforementioned lesions in the brain tissue of patients who have died with the disease or, rarely, in small biopsied samples of brain tissue taken during an invasive neurosurgical procedure.

Several lines of evidence indicate that progressive cerebral deposition of particular amyloidogenic proteins, β-amyloid proteins, (βAP), play a seminal role in the pathogenesis of AD and can precede cognitive symptoms by years or decades. See, Selkoe, (1991) Neuron 6:487. Recently, it has been shown that βAP is released from neuronal cells grown in culture and is present in cerebrospinal fluid (CSF) of both normal individuals and AD patients. See, Seubert et al., (1992) Nature 359:325-327.

A possible correlation to the plaque pathology has been developed by several groups demonstrating the direct βAP neurotoxicity toward, cultured neurons. Direct neurotoxicity of βAP was recently reported to be attenuated by co-treatment with TGF-β (Chao et al., Soc. Neurosci. Abs., 19:1251 (1993)).

More recently, in addition to the direct neurotoxicity, an inflammatory response in the AD brain, perhaps elicited by βAP, also contributes to the pathology of the disease. A limited clinical trial with the NSAID indomethacin exhibited a retardation in the progression of Alzheimer's dementia (Rogers et al., *Science*, 260:1719–1720 (1993)). European Patent Application 0659418 A1 describes the use of certain benzothiophenenes for the inhibition of Alzheimer's Disease.

Despite the progress that has been made in understanding the underlying mechanisms of AD, there remains a need to develop compositions and methods for treatment of these diseases. Treatment methods could advantageously be based on drugs which are capable of increasing TGF-β expression in the brain, thus ameliorating the β-amyloid peptide mediated neurotoxicity and inflammatory response associated with AD.

SUMMARY OF THE INVENTION

The present invention relates to methods for inhibiting Alzheimer's Disease comprising administering to a human in need of treatment an effective amount of a compound of formula I

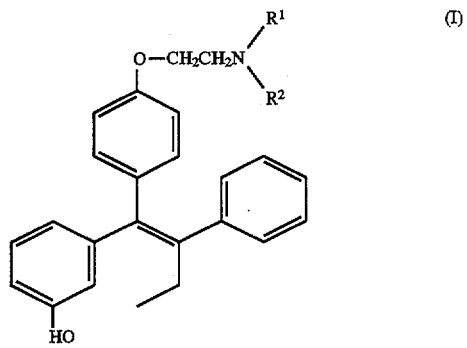

Wherein

R$^1$ and R$^2$ may be the same or different provided that, when R$^1$ and R$^2$ are the same, each is a methyl or ethyl group, and, when R$^1$ and R$^2$ are different, one of them is a methyl or ethyl group and the other is hydrogen or a benzyl group; or a pharmaceutically acceptable salt thereof. A preferred compound of formula I is that in which R$^1$ and R$^2$ are methyl. A preferred salt is the citrate salt.

DETAILED DESCRIPTION OF THE INVENTION

The present invention concerns methods for inhibiting Alzheimer's Disease. The term "inhibit" is defined to include its generally accepted meaning which includes prophylactically treating a subject to prevent the occurrence of one or more of these disease states, holding in check the symptoms of such a disease state, and/or treating such symptoms. Thus, the present methods include both medical therapeutic and/or prophylactic treatment, as appropriate.

The methods of this invention are practiced by administering to an individual in need of treatment an effective amount of a compound formula I

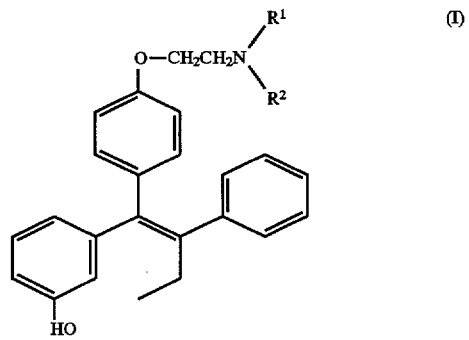

wherein

R$^1$ and R$^2$ may be the same or different provided that, when R$^1$ and R$^2$ are the same, each is a methyl or ethyl group, and, when $R^1$ and $R^2$ are different, one of them is a methyl or ethyl group and the other is hydrogen or a benzyl group; or a pharmaceutically acceptable salt thereof.

Compounds of formula I are known in the art and essentially are prepared via the methods described in U.S. Pat. No. 5,047,431, which is incorporated herein by reference.

A preferred formula I compound is that in which $R^1$ and $R^2$ each are methyl. This preferred compound is known as droloxifene, (E)-1-[4'-(2-Dimethylaminoethoxy)phenyl]-1-(3-hydroxyphenyl)-2-phenylbut-1-ene, which previously has been described as an antiestrogenic agent and is useful for the treatment of hormone dependent mammary tumors (U.S. Pat. No. 5,047,431), and for the relief of bone diseases caused by the deficiency of estrogen or the like (U.S. Pat. No. 5,254,594). Furthermore, droloxifene is known to have less uterotrophic effect than other antiestrogenic compounds such as tamoxifen.

Although the free-base form of formula I compounds can be used in the methods of the present invention, it is preferred to prepare and use a pharmaceutically acceptable salt form. Thus, the compounds used in the methods of this invention form pharmaceutically acceptable acid and base addition salts with a wide variety of inorganic and, preferably, organic acids and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the citrate salt.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

The pharmaceutically acceptable salts of formula I compounds generally have enhanced solubility characteristics compared to the compound from which they are derived, and thus are often more amenable to formulation as liquids or emulsions.

Once prepared, the free base or salt form of formula I compounds can be administered to an individual in need of treatment for the methods herein described. The following nonlimiting test examples illustrate the methods of the present invention.

For the methods of the present invention, compounds of Formula I are administered continuously, or from 1 to 4 times daily.

As used herein, the term "effective amount" means an amount of compound of the methods of the present invention which is capable of inhibiting the symptoms of the pathological conditions herein described. The specific dose of a compound administered according to this invention will, of course, be determined by the particular circumstances surrounding the case including, for example, the compound administered, the route of administration, the state of being of the patient, and the severity of the pathological condition being treated. A typical daily dose will contain a nontoxic dosage level of from about 0.25 mg to about 400 mg/day of a compound of the present invention. Preferred daily doses generally will be from about 1 mg to about 100 mg/day in one or two doses per day.

The compounds of this invention can be administered by a variety of routes including oral, rectal, transdermal, subcutaneous, intravenous, intramuscular, and intranasal. These compounds preferably are formulated prior to administration, the selection of which will be decided by the attending physician. Typically, a formula I compound, or a pharmaceutically acceptable salt thereof, is combined with a pharmaceutically acceptable carrier, diluent or excipient to form a pharmaceutical formulation.

The total active ingredients in such formulations comprises from 0.1% to 99.9% by weight of the formulation. By "pharmaceutically acceptable" it is meant the carrier, diluent, excipients, and/or salt must be compatible with the other ingredients of the formulation, and not deleterious to the recipient thereof.

Pharmaceutical formulations containing a compound of formula I can be prepared by procedures known in the art using well known and readily available ingredients. For example, the compounds of formula I can be formulated with common excipients, diluents, or carriers, and formed into tablets, capsules, suspensions, powders, and the like. Examples of excipients, diluents, and carriers that are suitable for such formulations include the following fillers and extenders such as starch, sugars, mannitol, and silicic derivatives binding agents such as carboxymethyl cellulose and other cellulose derivatives, alginates, gelatin, and polyvinyl-pyrrolidone; moisturizing agents such as glycerol; disintegrating agents such as calcium carbonate and sodium bicarbonate agents for retarding dissolution such as paraffin resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds also can be formulated as elixirs or solutions for convenient oral administration or as solutions appropriate for parenteral administration, for example, by intramuscular, subcutaneous or intravenous routes.

Additionally, the compounds are well suited to formulation as sustained release dosage forms and the like. The formulations can be so constituted that they release the active ingredient only or preferably in a particular physiological location, possibly over a period of time. The coatings, envelopes, and protective matrices may be made, for example, from polymeric substances or waxes.

Compounds of formula I generally will be administered in a convenient formulation. The following formulation examples only are illustrative and are not intended to limit the scope of the present invention.

In the formulations which follow, "active ingredient" means a compound of formula I, or a salt thereof.

FORMULATION 1: GELATIN CAPSULES

Hard gelatin capsules are prepared using the following:

| Ingredient | Quantity (mg/capsule) |
|---|---|
| Active ingredient | 0.25–100 |
| Starch, NF | 0–650 |
| Starch flowable powder | 0–50 |
| Silicone fluid 350 centistokes | 0–15 |

The formulation above may be changed in compliance with reasonable variations.

A tablet formulation is prepared using the ingredients below:

FORMULATION 2: TABLETS

| Ingredient | Quantity (mg/tablet) |
|---|---|
| Active ingredient | 0.25–100 |
| Cellulose, microcrystalline | 200–650 |
| Silicon dioxide, fumed | 10–650 |
| Stearate acid | 5–15 |

The components are blended and compressed to form tablets.

Alternatively, tablets each containing 0.25–100 mg of active ingredient are made up as follows:

FORMULATION 3: TABLETS.

| Ingredient | Quantity (mg/tablet) |
|---|---|
| Active ingredient | 0.25–100 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium, stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.25–100 mg of medicament per 5 ml dose are made as follows:

FORMULATIONS 4: SUSPENSIONS

| Ingredient | Quantity (mg/5 ml) |
|---|---|
| Active ingredient | 0.25–100 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified Water to | 5 mL |

The medicament is passed through a No. 45 mesh U.S. sieve and mixed with the sodium carboxymethyl cellulose and syrup to form smooth paste. The benzoic acid solution, flavor, and color are diluted with some of the water and added, with stirring. Sufficient water is then added to produce the required volume. An aerosol solution is prepared containing the following ingredients:

FORMULATION 5: AEROSOL

| Ingredient | Quantity (% by weight) |
|---|---|
| Active ingredient | 0.25 |
| Ethanol | 25.75 |
| Propellant 22 (Chlorodifluoromethane) | 70.00 |

The active ingredient is mixed with ethanol and the mixture added to a portion of the propellant 22, cooled to 30° C., and transferred to a filling device. The required amount is then fed to a stainless steel container and diluted with the remaining propellant. The valve units are then fitted to the container.

Suppositories are prepared as follows:

FORMULATION 6: SUPPOSITORIES

| Ingredient | Quantity (mg/suppository) |
|---|---|
| Active ingredient | 250 |
| Saturated fatty acid glycerides | 2,000 |

The active ingredient is passed through a No. 60 mesh U.S. sieve and suspended in the saturated fatty acid glycerides previously melted using the minimal necessary heat. The mixture is then poured into a suppository mold of nominal 2 g capacity and allowed to cool.

An intravenous formulation is prepared as follows:

FORMULATION 7: INTRAVENOUS SOLUTION

| Ingredient | Quantity |
|---|---|
| Active ingredient | 20 mg |
| Isotonic saline | 1,000 mL |

The solution of the above ingredients is intravenously administered to a patient at a rate of about 1 mL per minute.

Compounds of Formula I can be administered for prophylactic and/or therapeutic treatment of Alzheimer's Disease. In therapeutic applications, the compounds are administered to a host already suffering from a disease.

For prophylactic applications, the compounds of formula I are administered to a host susceptible to Alzheimer's Disease, but not necessarily already suffering from such disease. Such hosts may be identified by genetic screening and clinical analysis, as described in the medical literature, see e.g., Goate, *Nature*, 349:704–706 (1991). A preferred group for receiving compounds of the invention, either for prophylactic or therapeutic reasons, are post-menopausal women. (see e.g., Paganini-Hill, *Soc Neurosci Abs*, 19, 1046).

The particular dosage of a compound formula I according to this invention will depend upon the severity of the condition, the route of administration, and related factors that will be decided by the attending physician. Generally, accepted and effective daily doses will be from about 0.1 to about 100 mg/day, and more typically from about 10 to about 40 mg/day. Such dosages will be administered to a subject in need of treatment from once to about three times each day, or more often as needed, for a period of time sufficient to inhibit the effects of Alzheimer's Disease or its symptoms.

Frequently, it will be desirable or necessary to introduce the pharmaceutical compositions directly or indirectly to the brain. Direct techniques usually involve placement of a drug delivery catheter into the host's ventricular system to bypass the blood-brain barrier. Indirect techniques, which are generally preferred, involve formulating the compositions to provide for drug latentiation by the conversion of hydrophilic drugs into lipid soluble drugs. Latentiation is generally achieved through blocking of the hydroxyl, and amine groups present on the drug to render the drug more lipid soluble and amenable to transportation across the blood-brain barrier. Alternatively, the delivery of hydrophilic drugs can be enhanced by intra-arterial infusion of hypertonic solutions which can transiently open the blood-brain barrier.

It is usually preferred to administer a compound of formula I in the form of an acid addition salt, as is customary in the administration of pharmaceuticals bearing a basic group.

ASSAYS

Assays for compounds effective in treatment of AD are described in EP 0659418 A1.

Amylins may be purchased from Bachem, Inc. (Torrance, Calif.), Peninsula Laboratories, Inc. (Belmont, Calif.), Sigma Chemicals (St. Louis, Mo.). Amyloid-β(1–40) and reverse β-amyloid peptide (40–1) may be purchased from Bachem, Inc. microglobulin may be purchased from Sigma Chemicals (St. Louis, Mo.).

Stock solutions of peptides (1 mM) are freshly prepared in pyrogen-free sterile water and diluted to the indicated concentrations in defined culture media. Rat hippocampal cultures (10–14 days in vitro) are treated with peptides or vehicle for four days. The viability of the rat cortical cultures is visually assessed by phase contrast microscopy and quantified by measuring lactate dehydrogenase (LDH) released into the culture media.

Assay 1

Primary rat hippocampal neurons are cultured in vitro with standard cell culture techniques. Amyloid-beta (Aβ) peptide is added to cultured cells at a normally toxic concentration of 25–50 μM. After 4 days of treatment, viability is assessed by measurement of lactate dehydrogenase (LDH) released into culture medium. Lactate dehydrogenase (LDH) is measured in 20 μl aliquots of conditioned defined-DMEM using a standard 340 nm kinetic LDH assay (Sigma Catalog Number #228-20) in a 96 well format. Assays are performed at 37° C. in a PC-driven EL340 Microplate Biokinetics plate reader (Bio-Tek Instruments) using Delta Soft II software (v. 3.30B, BioMetallics, Inc.) for data analysis. Quality control standards containing normal and elevated levels of serum LDH (for example, Sigma Enzyme Controls 2N and 2E) are run with every assay. Results are expressed as units of LDH/L where 1 unit is defined as the amount of enzyme that will catalyze the formation of 1 micromole of nicotinamide adenine dinucleotide per minute under conditions of the assay. For protection studies, a compound of formula 1 is added to cultures prior to and/or concurrently with the amyloid-β treatment.

Activity of the compounds of formula 1 is illustrated by a decrease in LDH released into the media (a neurotoxic indicator), as compared to control.

Assay 2

Between five and fifty rats are subjected to 15 minutes of four vessel occlusion to induce global ischemia. A compound of the invention is administered to experimental and control animals prior to, concurrent with and/or up to several hours after 15 minutes of occlusion. Animals are sacrificed 3 days after the ischemic insult and neuronal damage in the hippocampus and striatum is then visually assessed by standard histologic techniques.

Activity of the compounds of formula 1 is illustrated by a decrease in neuronal damage.

Assay 3

Five to fifty women are selected for the clinical study. The women are post-menopausal, i.e., have ceased menstruating for between 6 and 12 months prior to the study's initiation, have been diagnosed with early stage Alzheimer's Disease (AD), are expected to have worsening symptoms of AD within the study period, but are in good general health otherwise. The study has a placebo control group, i.e., the women are divided into two groups, one of which receives the active agent of this invention and the other receives a placebo. The patients are benchmarked as to memory, cognition, reasoning, and other symptoms associated with AD. Women in the test group receive between 10–100 mg of the active agent per day by the oral route. They continue this therapy for 6–36 months. Accurate records are kept as to the benchmarked symptoms in both groups and at the end of the study these results are compared. The results are compared both between members of each group and also the results for each patient are compared to the symptoms reported by each patient before the study began. Activity of the test drug is illustrated by an attenuation of the typical cognitive decline and/or behavioral disruptions associated with AD.

Utility of the compounds of formula I is evidenced by activity in at least one of the above assays.

I claim:

1. A method for inhibiting Alzheimer's Disease comprising administering to a human in need of (such) said treatment an effective amount of a compound of formula I

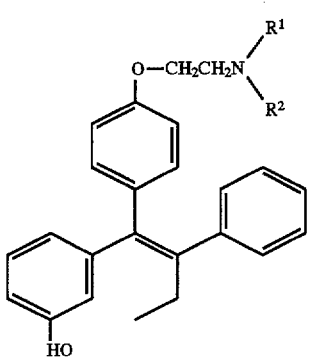

(I)

wherein

R¹ and R² may be the same or different provided that, when R¹ and R² are the same, each is a methyl or ethyl group, and, when R¹ and R² are different, one of them is a methyl or ethyl group and the other is hydrogen or (a) benzyl (group); or a pharmaceutically acceptable salt thereof.

2. A method according to claim 1 wherein the compound of formula I is a compound wherein R¹ and R² each are methyl, or a pharmaceutically acceptable salt thereof.

3. A method according to claim 2 wherein said salt is the citrate salt.

* * * * *